United States Patent

Matsuzaki et al.

[11] 4,324,801
[45] Apr. 13, 1982

[54] PHENYLGUANIDINE ACETYLSALICYLATE COMPOUNDS, PROCESS FOR PRODUCTION THEREOF, AND PHARMACEUTICAL COMPOSITION THEREOF

[75] Inventors: Meiki Matsuzaki, Hachioji; Hiroshi Okabe, Yokohama; Seishiro Tanaka, Sendai; Takao Takiguchi, Tokyo; Kunikatsu Onodera, Chiba, all of Japan

[73] Assignee: Banyu Pharmaceutical Co. Ltd., Tokyo, Japan

[21] Appl. No.: 256,165

[22] Filed: Apr. 21, 1981

[51] Int. Cl.$^3$ .............. C07C 101/00; C07C 69/157; C07C 51/02; A61K 31/155; A61K 31/19; A61K 31/615

[52] U.S. Cl. .............................. 424/311; 560/34; 560/143

[58] Field of Search ............... 560/34, 143; 424/311

[56] References Cited

U.S. PATENT DOCUMENTS 4,218,445  8/1980  Thirumalachar et al. .......... 560/143

*Primary Examiner*—Natalie Trousof
*Assistant Examiner*—Frederick W. Pepper

*Attorney, Agent, or Firm*—Sherman and Shalloway

[57] ABSTRACT

A compound of the formula

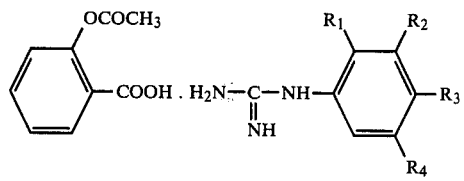

wherein $R_1$ is a member selected from the group consisting of a hydrogen atom, lower alkyl groups and lower alkoxy groups, $R_2$ is a member selected from the group consisting of a hydrogen atom, halogen atoms, lower alkyl groups, a hydroxyl group and a trifluoromethyl group, $R_3$ is a member selected from the group consisting of a hydrogen atom, halogen atoms, lower alkyl groups, lower alkoxy groups, an acetyl group, a carbamoyl group and lower alkyl carboxylate groups, and $R_4$ represents a hydrogen atom or a halogen atom, a pharmaceutical composition comprising such a phenylguanidine acetylsalicylate compound as an active ingredient; and a process for production of aforesaid compound.

7 Claims, No Drawings

PHENYLGUANIDINE ACETYLSALICYLATE COMPOUNDS, PROCESS FOR PRODUCTION THEREOF, AND PHARMACEUTICAL COMPOSITION THEREOF

This invention relates to phenylguanidine acetylsalicylate compounds not described in the literature, a process for production thereof, and to a pharmaceutical composition comprising such a phenylguanidine acetylsalicylate compound.

Salicylic acid and acetylsalicylic acid have already been used as antipyretic, analgesic and anti-inflammatory agents. But they have low water solubility and may induce side-effects such as gastrointestinal troubles at large doses. The water solubility of acetylsalicylic acid may be increased by converting it to an alkali metal salt, but the alkali metal salt has the defect that it is easily deacetylated to the alkali metal salicylate.

The present inventors made investigations in order to provide a compound which is free from such a trouble or defect, and succeeded in synthesizing many salts of acetylsalicylic acid and guanidines as a base which are not described in the literature. Examination of these salts has finally led to the discovery that phenylguanidine acetylsalicylate compounds of the following formula

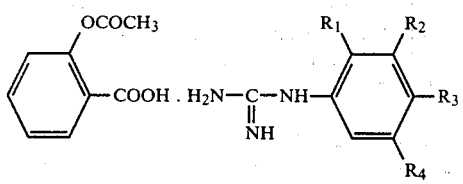

wherein $R_1$ is a member selected from the group consisting of a hydrogen atom, lower alkyl groups and lower alkoxy groups, $R_2$ is a member selected from the group consisting of a hydrogen atom, halogen atoms, lower alkyl groups, a hydroxyl group and a trifluoromethyl group, $R_3$ is a member selected from the group consisting of a hydrogen atom, halogen atoms, lower alkyl groups, lower alkoxy groups, an acetyl group, a carbamoyl group and lower alkyl carboxylate groups, and $R_4$ represents a hydrogen atom or a halogen atom, have a higher solubility in water than acetylsalicylic acid, and possess high pharmacological activities which make them useful as antipyretic-analgesic agents, anti-inflammatory agents, platelet aggregation inhibitors and prostaglandin formation inhibitors. It has also been found that these compounds of formula (I) can be formulated into injectable solutions applicable both intravenously and intramuscularly, and in oral administration, too, they cause much less gastrointestinal troubles than acetylsalicylic acid because their hydrogen ion concentration is close to neutrality.

It is an object of this invention therefore to provide novel phenylguanidine acetylsalicylate compounds.

Another object of this invention is to provide a process for producing these compounds, and a pharmaceutical composition comprising such a compound as an active ingredient.

Still another object of this invention is to provide a pharmaceutical composition comprising such a phenylguanidine acetylsalicylate compound as an active ingredient.

The above and other objects and advantages of this invention will become more apparent from the following description.

The compounds of formula (I) can be easily obtained by reacting a guanidine salt of the following formula which can be obtained by a method known per se, for example the method described in Charles E. Braun, J. Am. Chem. Soc., vol. 55, p. 1281 (1933)

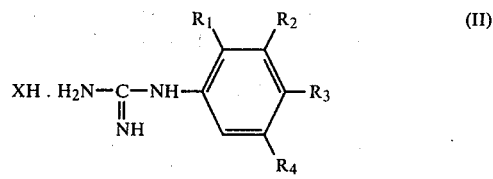

wherein $R_1$, $R_2$, $R_3$ and $R_4$ are as defined hereinabove, and XH represents a hydrohalic acid, sulfuric acid or carbonic acid,
with acetylsalicylic acid.

The reaction can be carried out easily by contacting the compound of formula (II) as a free base with acetylsalicylic acid in a solvent such as anhydrous ethanol, chloroform or acetone, as illustrated in Examples to be given hereinbelow. The reaction proceeds easily at room temperature, and no cooling or heating is required in particular. The product can be further purified by recrystallization from acetone, a mixture of acetone and ligroin, etc., as shown in the Examples.

Preferred compounds of formula (I) which can be obtained in the aforesaid manner include compounds of formula (I) in which $R_1$ is a member selected from the group consisting of a hydrogen atom, a methyl group and a methoxy group, especially preferably a hydrogen atom or a methyl group; $R_2$ is a member selected from the group consisting of a hydrogen atom, a chlorine atom, a methyl group, a hydroxyl group and a trifluoromethyl group, especially preferably a hydrogen atom or a methyl group; $R_3$ is a member selected from the group consisting of a hydrogen atom, a chlorine atom, a methyl group $C_1$–$C_2$ alkoxy groups, an acetyl group, a carbamoyl group and an ethoxycarbonyl group, especially preferably a hydrogen atom, a methyl group or a $C_1$–$C_2$ alkoxy group; and $R_4$ is a hydrogen atom or a chlorine atom, especially preferably a hydrogen atom.

Examples of especially preferred compounds of formula (I) are 2-methylphenylguanidine acetylsalicylate, 3-methylphenylguanidine acetylsalicylate, 4-methylphenylguanidine acetylsalicylate, 3,4-dimethylphenylguanidine acetylsalicylate, 4-methoxyphenylguanidine acetylsalicylate, and 4-ethoxyphenylguanidine acetylsalicylate.

The compounds of formula (I) are useful as antipyretic-analgesic agents, anti-inflammatory agents, platelet aggregation inhibitors, and prostaglandin formation inhibitors. Accordingly, the present invention can provide a pharmaceutical composition comprising an antipyretically and analgesically effective amount of a compound of formula (I) and a pharmaceutically acceptable carrier or diluent; a pharmaceutical composition comprising an anti-inflammatorily effective amount of a compound of formula (I) and a pharmaceutically acceptable carrier or diluent; a pharmaceutical composition comprising an amount, effective for inhibition of platelet aggregation, of a compound of formula (I) and a pharmaceutically acceptable carrier or diluent; and a pharmaceutical composition comprising an amount, effective for inhibition of prostaglandin formation, of a compound of formula (I) and a pharmaceutically acceptable carrier or diluent.

The pharmaceutically acceptable carrier or diluent used in preparing such pharmaceutical compositions is known, and may include known carriers or diluents used in preparing various known pharmaceutical preparations such as powders, granules, tablets, capsules and injectable preparations. For example, they include solid carriers or diluents such as lactose, glucose, starch, magnesium carbonate and capsules, and liquid carriers or diluents such as distilled deionized water, Ringer's solution, infusions and an isotonic sodium chloride solution.

The effective amount of the compound of formula (I) in the above pharmaceutical compositions is from about 0.5 to about 60% by weight. The dose of the pharmaceutical compositions of this invention, as can be derived from the results of tests shown in the Examples, is, for example, about 5 to about 30 mg of the active ingredient/kg for antipyretic and analgesic purposes, about 5 to about 30 mg of the active ingredient/kg for anti-inflammatory purposes, about 3 to about 10 mg of the active ingredient/kg for inhibiting platelet aggregation, and about 2 to about 5 mg of the active ingredient/kg for inhibiting prostaglandin formation, when the pharmaceutical compositions are in the form of powders, granules, tablets and capsules. When the compositions are in the form of an injectable preparation, the dose is, for example, about 0.5 to about 3 mg/kg for antipyretic and analgesic purposes, about 0.5 to about 3 mg/kg for anti-inflammatory purposes, about 0.3 to about 1 mg/kg for inhibiting platelet aggregation, and about 0.2 to about 0.5 mg/kg for inhibiting prostaglandin formation.

As the Examples show, the active ingredients in accordance with this invention are low in toxicity.

The following Examples illustrate the present invention more specifically.

EXAMPLE 1

2-Methylphenylguanidine acetylsalicylate:

3.7 g of 2-methylphenylguanidine hydrochloride was dissolved in 150 ml of anhydrous ethanol, and 0.46 g of metallic sodium was added to the solution. The mixture was stirred at room temperature until the metallic sodium dissolved completely. The resulting precipitate was removed by filtration, and the excess of ethanol was distilled off. The residue was extracted with benzene to give 2.8 g of free guanidine. It was then dissolved in 100 ml of chloroform and 3.2 g of acetylsalicylic acid was added. The mixture was stirred at room temperature for 3 hours. After the reaction, chloroform was distilled off, and the residue was recrystallized from acetone.
Melting point: 127.5° to 128.5° C.
Amount yielded: 2.5 g (42.7%)

EXAMPLE 2

4-Methoxyphenylguanidine acetylsalicylate:

4.0 g of 4-methoxyphenylguanidine hydrochloride was treated with metallic sodium in anhydrous ethanol. The resulting precipitate was removed by filtration, and the excess of ethanol was distilled off. The residue was extracted with benzene. Benzene was distilled off, and the residue was dissolved in 150 ml of chloroform, and 3.2 g of acetylsalicylic acid was added. The mixture was stirred at room temperature for 3 hours. After the reaction, chloroform was distilled off, and the residue was recrystallized from a mixture of acetone and ligroin.
Melting point: 134° to 135° C.
Amount yielded: 4.2 g (68.3%)

EXAMPLE 3

4-Carbamoylphenylguanidine acetylsalicylate:

5.5 g of 4-carbamoylphenylguanidine hydrochloride was dissolved in water, and an equivalent weight of sodium hydroxide was added, whereupon crystals precipitated. The crystals were collected by filtration, dried, and then suspended in 250 ml of acetone. The suspension was stirred at room temperature, and 4.2 g of acetylsalicylic acid was added. The crystals immediately dissolved, and then white crystals precipitated. Stirring was continued for 3 hours. After the reaction, the crystals were collected by filtration, well washed with acetone and then with ether, and dried.
Melting point: 165° to 166° C.
Amount yielded: 7.7 g (93.4%)

EXAMPLE 4

3-Hydroxy-4-carboethoxyphenylguanidine acetylsalicylate:

4.8 g of 3-hydroxy-4-carboethoxyphenylguanidine was suspended in 200 ml of chloroform, and 3.9 g of acetylsalicylic acid was added. The mixture was stirred at room temperature for 3 hours. After the reaction, the reaction mixture was cooled, and the resulting crystals were collected by filtration. The crystals were then recrystallized from a mixture of acetone and ligroin.
Melting point: 122° to 124° C.
Amount yielded: 5.9 g (67.8%)

Some examples of the novel compounds of formula (I) are tabulated below together with their physical constants. These examples are merely illustrative and do not in any way limit the scope of the invention. The structures of the novel compounds of formula (I) are determined by elemental analysis, infrared absorption spectroscopy, and proton nuclear magnetic resonance spectroscopy.

TABLE 1

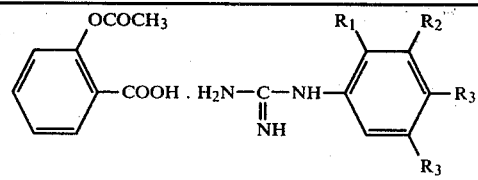

| | $R_1$ | $R_2$ | $R_3$ | $R_4$ | melting point (°C) |
|---|---|---|---|---|---|
| 1 | H | H | H | H | 135.5–136.5 |
| 2 | CH$_3$ | H | H | H | 127.5–128.5 |
| 3 | H | CH$_3$ | H | H | 116–118 |
| 4 | H | H | CH$_3$ | H | 125.5–126.5 |
| 5 | H | CH$_3$ | CH$_3$ | H | 143–144.5 |
| 6 | H | Cl | CH$_3$ | H | 116–117.5 |
| 7 | CH$_3$ | H | Cl | H | 122–123 |
| 8 | H | H | Cl | H | 122–123 |
| 9 | H | Cl | H | H | 122–123 |
| 10 | OCH$_3$ | H | H | H | 111–113 |
| 11 | H | H | OCH$_3$ | H | 134–135 |
| 12 | OCH$_3$ | H | H | Cl | 144.5–145 |
| 13 | H | H | OC$_2$H$_5$ | H | 127–128 |
| 14 | H | H | COCH$_3$ | H | 125–126 |
| 15 | H | CF$_3$ | H | H | 138–139 |
| 16 | H | H | CONH$_2$ | H | 165–166 |
| 17 | H | OH | COOC$_2$H$_5$ | H | 122–124 |

The pharmacological activities, toxicities and side-effects of the compounds of formula (I) were tested as follows:

1. Anti-inflammatory activity

Male guinea pigs having a body weight of about 350 g were used. The back hair of each guinea pig was removed, and ultraviolet light was irradiated onto the back. Each of the compounds shown in Table 1 was administered orally one hour before the irradiation, or intraperitoneally 30 minutes before the irradiation, and the degrees of inflammation were compared using aspirin and mefenamic acid as controls. The results are shown in Table 2.

TABLE 2

| Compound | $ED_{50}$ (mg/kg) Oral |
|---|---|
| 1 | 140 |
| 2 | 65 |
| 3 | 110 |
| 4 | 90 |
| 5 | 85 |
| 6 | 35 |
| 7 | 40 |
| 8 | 25 |
| 9 | 180 |
| 10 | 95 |
| 11 | 95 |
| 12 | 95 |
| 13 | 85 |
| 14 | 85 |
| 15 | 100 |
| 16 | 200 |
| 17 | — |
| Aspirin | 90 |
| Mefenamic acid | 30 |

2. Antipyretic-analgesic activity (1) Antipyretic activity

Male rats having a body weight of 200 to 250 g were used. Rises in body temperature (the temperature of the rectum) were induced by subcutaneous injection of 5% peptone (0.5 ml/100 g body weight), and the antipyretic activity of each of the compounds was compared with those of aspirin and mefenamic acid as a control. The results are shown in Table 3.

TABLE 3

| Compound | Inhibiting ratio (%)(*) |
|---|---|
| 1 | 74.1 |
| 2 | 88.1 |
| 3 | 28.0 |
| 4 | 83.9 |
| 5 | 30.1 |
| 6 | 2.1 |
| 7 | 90.9 |
| 8 | 30.1 |
| 9 | 88.1 |
| 10 | 32.2 |
| 11 | 25.2 |
| 12 | 83.9 |
| 13 | 62.9 |
| 14 | 51.0 |
| 15 | 100 |
| 16 | 72.0 |
| 17 | — |
| Aspirin | 81.0 |
| Mefenamic acid | 79.0 |

(*)Inhibiting ratio against the control in oral administration at a dose of 200 mg/kg (rat).

(2) Analgesic activity

The analgesic activity was tested by the acetic acid writhing method. Male mice having a body weight of 18 to 20 g were used. Each of the compounds shown in Table 1 was administered orally, intravenously and intraperitoneally, and then 0.2 ml of a 0.7% aqueous solution of acetic acid was administered intraperitoneally 60 minutes (in oral administration), 10 minutes (in intravenous administration), and 15 minutes (in intraperitoneal administration) after the administration of the test compounds. The number of writhings which were observed from 5 minutes after the administration of acetic acid to 25 minutes was counted, and compared against aspirin and mefenamic acid as a control. In comparison with the controls, a marked analgesic activity was noted in compound No. 5, but the other compounds did not show a significant difference from the controls.

3. Inhibition of platelet aggregation

This was measured by the method of Born et al. Specifically, using collagen as an aggregation inducer, each of the compounds shown in Table 1 was tested to measure the inhibition of platelet aggregation in rabbit's platelet-rich plasma (PRP). Aspirin and mefenamic acid were used as controls. The results are shown in Table 4.

TABLE 4

| Compound | $IC_{50}$ (μg/ml)(*) |
|---|---|
| 1 | 6.0 |
| 2 | 10.5 |
| 3 | 7.0 |
| 4 | 4.5 |
| 5 | 2.0 |
| 6 | 5.7 |
| 7 | 2.5 |
| 8 | 9.2 |
| 9 | 5.2 |
| 10 | >20 |
| 11 | 9.6 |
| 12 | 10.8 |
| 13 | 12.2 |
| 14 | 8.8 |
| 15 | >20 |
| 16 | 12.5 |
| 17 | — |
| Aspirin | 12.6 |
| Mefenamic acid | >20 |

(*)Final concentration at 50% inhibition of platelet aggregation.

4. Inhibition of prostaglandin synthesis

Each of the compounds shown in Table 1 was tested to measure the inhibition of prostaglandin synthesis in a washed platelet suspension by measuring the malondialdehyde formation following the addition of arachidonic acid in vitro. Aspirin and mefenamic acid were used as controls. The results are shown in Table 5.

TABLE 5

| Compound | $IC_{50}$ (μg/ml)(*) |
|---|---|
| 1 | 4.3 |
| 2 | 3.4 |
| 3 | 3.7 |
| 4 | 2.4 |
| 5 | 4.8 |
| 6 | 1.9 |
| 7 | 4.1 |
| 8 | 4.7 |
| 9 | 5.0 |
| 10 | 4.1 |
| 11 | 3.3 |
| 12 | 4.1 |
| 13 | 4.0 |
| 14 | 4.6 |
| 15 | 5.2 |
| 16 | 4.5 |
| 17 | — |
| Aspirin | 2.4 |
| Mefenamic acid | 1.4 |

(*)Final concentration at 50% inhibition of malondialdehyde formation.

5. Acute toxicity and influences on the stomach and intestines (1) Acute toxicity The LD$_{50}$ (50% lethal doses) in mice of each of the compounds shown in Table 1 and aspirin and mefenamic acid were measured, and are shown in Table 6.

TABLE 6

| Compound | LD$_{50}$ (mg/kg) oral |
| --- | --- |
| 1 | 400 |
| 2 | 400 |
| 3 | 400 |
| 4 | 600 |
| 5 | 300 |
| 6 | 400 |
| 7 | 1600 |
| 8 | 1100 |
| 9 | 800 |
| 10 | 800 |
| 11 | 300 |
| 12 | 1200 |
| 13 | 600 |
| 14 | 600 |
| 15 | 800 |
| 16 | 1600 |
| 17 | 1100 |
| Aspirin | 950 |
| Mefenamic acid | 800 |

(2) Influences on the stomach and intestines

The influences of each of the compounds shown in Table 1 on the stomach and intestines were determined against aspirin and mefenamic acid as controls 6 and 14 hours respectively after oral administration. It was found that the compounds tested cause little gastrointestinal troubles, or even where they caused gastrointestinal troubles, the degree of such troubles was less than those induced by aspirin and mefenamic acid. No trouble to the liver and kidneys was noted.

What we claim is:

1. A compound of the formula

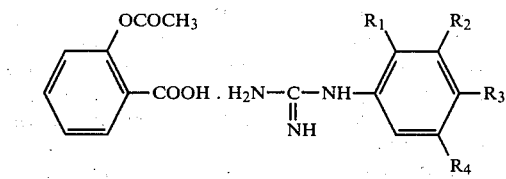

wherein R$_1$ is a member selected from the group consisting of a hydrogen atom, lower alkyl groups and lower alkoxy groups, R$_2$ is a member selected from the group consisting of a hydrogen atom, halogen atoms, lower alkyl groups, a hydroxyl group and a trifluoromethyl group, R$_3$ is a member selected from the group consisting of a hydrogen atom, halogen atoms, lower alkyl groups, lower alkoxy groups, an acetyl group, a carbamoyl group and lower alkyl carboxylate groups, and R$_4$ represents a hydrogen atom or a halogen atom.

2. The compound of claim 1 wherein R$_1$ is a member selected from the group consisting of a hydrogen atom, a methyl group and a methoxy group, R$_2$ is a member selected from the group consisting of a hydrogen atom, a chlorine atom, a methyl group, a hydroxyl group and a trifluoromethyl group, R$_3$ is a member selected from the group consisting of a hydrogen atom, a chlorine atom, a methyl group, C$_1$–C$_2$ alkoxy groups, an acetyl group, a carbamoyl group and an ethoxycarbonyl group, and R$_4$ represents a hydrogen atom or a chlorine atom.

3. The compound of claim 2 wherein R$_1$ is a hydrogen atom or a methyl group, R$_2$ is a hydrogen atom or a methyl group, R$_3$ is a hydrogen atom, a methyl group or an alkoxy group having 1 or 2 carbon atoms, and R$_4$ is a hydrogen atom.

4. A pharmaceutical composition composed of an anti-inflammatorily effective amount or an antipyretically and analgesically effective amount of a compound of the formula

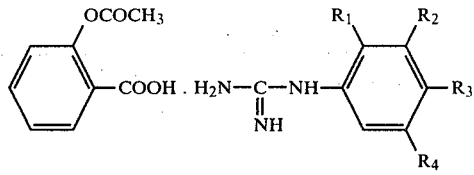

wherein R$_1$ is a member selected from the group consisting of a hydrogen atom, lower alkyl groups and lower alkoxy groups, R$_2$ is a member selected from the group consisting of a hydrogen atom, halogen atoms, lower alkyl groups, a hydroxyl group and a trifluoromethyl group, R$_3$ is a member selected from the group consisting of a hydrogen atom, halogen atoms, lower alkyl groups, lower alkoxy groups, an acetyl group, a carbamoyl group and lower alkyl carboxylate groups, and R$_4$ represents a hydrogen atom or a halogen atom; and a pharmaceutically acceptable carrier or diluent.

5. A pharmaceutical composition composed of an amount, effective for inhibiting platelet aggregation, of a compound of the formula

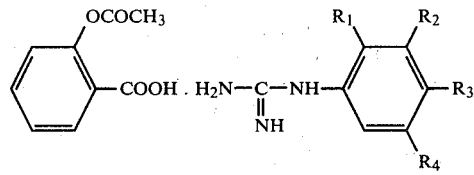

wherein R$_1$ is a member selected from the group consisting of a hydrogen atom, lower alkyl groups and lower alkoxy groups, R$_2$ is a member selected from the group consisting of a hydrogen atom, halogen atoms, lower alkyl groups, a hydroxyl group and a trifluoromethyl group, R$_3$ is a member selected from the group consisting of a hydrogen atom, halogen atoms, lower alkyl groups, lower alkoxy groups, an acetyl group, a carbamoyl group and lower alkyl carboxylate groups, and R$_4$ represents a hydrogen or halogen atom; and a pharmaceutically acceptable carrier or diluent.

6. A pharmaceutical composition composed of an amount, effective for inhibiting prostaglandin formation, of a compound of the formula

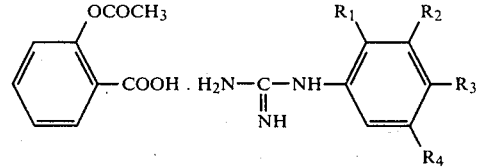

wherein R$_1$ is a member selected from the group consisting of a hydrogen atom, lower alkyl groups and lower alkoxy groups, $R_2$ is a member selected from the group consisting of a hydrogen atom, halogen atoms, lower alkyl groups, a hydroxyl group and a trifluoromethyl group, $R_3$ is a member selected from the group consisting of a hydrogen atom, halogen atoms, lower alkyl groups, lower alkoxy groups, an acetyl group, a carbamoyl group and lower alkyl carboxylate groups, and $R_4$ represents a hydrogen or halogen atom; and a pharmaceutically acceptable carrier of diluent.

7. A compound selected from the group consisting of 2-methylphenylguanidine acetylsalicylate, 3-methylphenylguanidine acetylsalicylate, 4-methylphenylguanidine acetylsalicylate, 3,4-dimethylphenylguanidine acetylsalicylate, 4-methoxyphenylguanidine acetylsalicylate, and 4-ethoxyphenylguanidine acetylsalicylate.

* * * * *